US006442427B1

United States Patent
Boute et al.

(10) Patent No.: US 6,442,427 B1
(45) Date of Patent: Aug. 27, 2002

(54) METHOD AND SYSTEM FOR STIMULATING A MAMMALIAN HEART

(75) Inventors: Willem Boute, Dieren; Harm H. Van Bolhuis, Warmond, both of (NL)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 09/559,048

(22) Filed: Apr. 27, 2000

(51) Int. Cl.[7] .............................................. A61N 1/362
(52) U.S. Cl. ......................................................... 607/9
(58) Field of Search ........................................ 607/9, 5

(56) References Cited

U.S. PATENT DOCUMENTS

| | | | |
|---|---|---|---|
| 3,937,266 A | 2/1976 | Cordone et al. ................ 164/9 |
| 4,088,140 A | 5/1978 | Rockland et al. ...... 128/419 PG |
| 4,332,259 A | 6/1982 | McCorkle, Jr. .............. 128/786 |
| 4,354,497 A | 10/1982 | Kahn ..................... 128/419 D |
| 4,458,677 A | 7/1984 | McCorkle et al. .......... 128/786 |
| 4,548,203 A | 10/1985 | Tacker, Jr. et al. ...... 128/419 D |
| 4,928,688 A | * 5/1990 | Mower |
| 5,174,289 A | 12/1992 | Cohen .................. 128/419 PG |
| 5,267,560 A | 12/1993 | Cohen .......................... 607/25 |
| 5,514,161 A | 5/1996 | Limousin ........................ 607/9 |
| 5,584,867 A | 12/1996 | Limousin et al. .............. 607/9 |
| 5,674,259 A | * 10/1997 | Gray |

OTHER PUBLICATIONS

Daubert et al, "Permanent Atrial Resynchronization by synchronous bi–strial Pacing in the Preventive Treatment of Atrial Flutter Associated with High Degree Interatrial Block", Arch Mal Coeur Vaiss, 1994 Nov. 1987 (11 Suppl), pp. 1535–1546.

Daubert et al, Permanent Dual Atrium Pacing in Major Intratrial Conduction Blocks: a four years experience. PACE (vol. 16. Part II) Naspe abstract 141, p. 885, Apr. 1993.

Daubert et al, "Permanent Left Ventricular Pacing with transvenous Leads inserted into the coronary veins" PACE (vol. 21 Part II) p. 239–245, Jan. 1998.

Cazeau et al, "Four Chamber Pacing in Dilated Cardiomyopathy" PACE (vol.17 Part II), p.1974–1979, Nov. 1994.

Daubert et al. Renewal of Permanent Left Atrial Pacing via the Coronary Sinus: PACE (vol. 15, Part II) NASPE Abstract 255 p. 572, Apr. 1992.

Olson et al. "Onset and Stability for Ventricular Tachyarrhythmia Detection in an Implantable Pacer–Cardioverter–Defibrillator" Computers in Cardiology, Oct. 7–10, 1986, IEEE Computer Society Press, p. 167–170.

Arzbaecher et al. "Automatic Tachycardia Recognition" PACE May/Jun. 1984, p. 541–547.

Papageorgiou et al, "Coronary Sinus Pacing Prevents Induction of Atrial Fibrillation", Circulation, 1997, Sep. 16, vol. 96, No.6, pp. 1893–1898.

"Diva Functional Product Description" by Vitatron (product description of a PVC synchronous pacing device).

* cited by examiner

Primary Examiner—Scott M. Getzow
(74) Attorney, Agent, or Firm—Thomas F. Woods; Thomas G. Berry

(57) ABSTRACT

A method for instantaneously stimulating a mammalian heart is provided. The mammalian heart includes a first atrium and a second atrium. A commencement signal is received. At least one additional signal is received. A plurality of intervals corresponding to the time between two successive signals is measured. An average interval is calculated. One of the plurality of intervals is compared to the average interval. Finally, a contraction signal is instantly transmitted to the second atrium when a difference between the average interval and one of the plurality of intervals is greater than a predetermined time period, instantaneously transmitting a contraction signal to the second atrium.

50 Claims, 6 Drawing Sheets

METHOD AND SYSTEM FOR STIMULATING A MAMMALIAN HEART

FIELD OF THE INVENTION

The present invention relates to cardial pacing systems, and, in particular, to cardial pacing systems providing for the immediate contractual stimulation of an atrium of a mammalian heart upon the detection of a premature atrial contraction in a second atrium.

BACKGROUND OF THE INVENTION

The cardiovascular system provides oxygenated blood to various structures of the body. In a normally functioning heart, the body's demand for oxygenated blood varies, and the heart responds by increasing or decreasing its rate and force of contraction to meet the demand. An electrical signal generated by the sinus node in the upper right atrial wall near the base of the heart is transmitted through the two upper heart chambers, i.e., the right and left atria, which causes them to synchronously contract. The contraction of the two upper heart chambers forces blood, pooled within the chambers, through open heart valves and into the right and left ventricles, the two lower heart chambers. The atrial electrical depolarization wave arrives at the atrio-ventricular (AV) node, superior to the ventricles, and triggers the conduction of a ventricular depolarization wave down the bundle of His in the septum between the right and left ventricles to the apex of the heart. The two ventricles contract after a brief AV delay time following the sinus node depolarization as the depolarization wave then advances superiorly, posteriorly, and anteriorly throughout the outer ventricular wall of the heart. The two lower heart chambers contract and force the blood through the vascular system of the body. The contraction of the right and left ventricles then proceeds in an organized fashion which optimizes the emptying of the ventricular chambers. The synchronous electrical depolarization of the atrial and ventricular chambers can be electrically sensed and displayed, and the electrical waveform is characterized by accepted convention as the "PQRST" complex. The PQRST complex includes the P-wave, which corresponds to the atrial depolarization wave; the R-wave, corresponding to the ventricular depolarization wave; and the T-wave, which represents the re-polarization of the cardiac cells.

Various disease mechanisms may cause conduction disturbances which interfere with the natural conduction system of the heart and affect the heart's ability to provide adequate cardiac output to the body. In certain disease mechanisms, the sinus node may fail to depolarize and commence the P-wave as rapidly as required to satisfy the demand for oxygenated blood, or the atria themselves may spontaneously depolarize at rates that are well in excess of the ability of the ventricles to respond. In such situations, the ventricles may compensate by depolarizing spontaneously from ectopic depolarization sites. In other cases in which the sinus node operates correctly, 1:1 atrial and ventricular depolarization synchrony is lost because the AV node may fail to respond to the P-waves or a defect in the bundle of His interferes with the conduction of the ventricular depolarization. In these cases, the ventricles may contract at a rate inadequate for providing sufficient cardiac output.

When either the atria or ventricles contract too slowly, the patient may be a candidate for implantation of a cardiac pacemaker for restoring the heart rate by applying pacing pulses to the heart chamber that is malfunctioning at a pacing rate that restores adequate cardiac output. Modern implantable cardiac pacemakers comprise an implantable pulse generator (IPG) and a lead or leads extending from the IPG to pace/sense electrode or electrodes located with respect to the heart chamber to deliver the pacing pulses and/or sense the P-wave or R-wave. Typically, the leads are transvenously introduced into the particular heart chamber via the superior vena cava and right atrium, and the pace/sense electrodes are maintained in contact with the heart tissue by a fixation mechanism at the distal end of the lead. However, leads may be placed subcutaneously between the IPG and the exterior or the heart, and the pace/sense electrodes attached to the epicardium at the desired sites. Moreover, enocardial coronary sinus leads are introduced through the right atrium into the coronary sinus and the great vein to locate pace/sense electrodes in proximity to the left atrium or the left ventricle.

A single chamber, demand pacemaker may be implanted into the patient to supply pacing pulses to a single upper or lower heart chamber, typically the right atrium or right ventricle, in response to bradycardia of the same chamber. In an atrial demand pacemaker operating in an AAI pacing mode, an atrial pacing pulse is delivered to the atrial pace/sense electrodes by the IPG if a P-wave is not sensed by an atrial sense amplifier coupled to the artial pace/sense electrodes within an atrial escape interval (A-A interval) timed by an atrial escape interval timer. In a ventricular demand pacemaker operating in a VVI pacing mode, a ventricular pacing pulse to the ventricular pace/sense electrodes if an R-wave is not sensed by a ventricular sense amplifier coupled to the ventricular pace/sense electrodes within a ventricular escape interval (V-V interval) timed by a ventricular escape interval timer.

Additionally, a dual chamber, demand pacemaker may be implanted into the patient to supply pacing pulses, when required, to one upper heart chamber and to one lower heart chamber, typically the right atrium and the right ventricle. In a dual chamber, demand pacemaker operating in a DDD pacing mode, both the AAI and VVI modes are followed, under the above defined conditions. A ventricular pacing pulse is delivered to the ventricular pace/sense electrodes if an R-wave is not sensed by the ventricular sense amplifier coupled thereto within an AV time interval timed from the sensing of a P-wave by the atrial sense amplifier.

Over the years, it has been proposed that various conduction disturbances involving both the bradycardia and the tachycardia of the heart chamber could benefit from stimulation applied at multiple electrode sites positioned in or about it in synchrony with a depolarization which has been sensed at least one of the electrodes sites. In addition, it has been proposed to employ pacing to compensate for conduction defects and in congestive heart failure where depolarizations that naturally occur in one upper or lower chamber are not conducted quickly enough to the other upper or lower heart chamber. In such cases, the right and left heart chambers do not contract in optimum synchrony with each other, and the cardiac output suffers due to the timing imbalance. In other cases, spontaneous depolarizations of the left atrium or left ventricle occur at ectopic foci in these left heart chambers, and the natural activation sequence is grossly disturbed. In such cases, cardiac output deteriorates because the contraction of the right and left heart cambers are not synchronized sufficiently to eject blood therefrom.

In patients suffering from congestive heart failure, the hearts become dilated and the conduction and depolarization sequences of the heart chambers may exhibit Intra-Atrial Conduction Defects (IACD), Left Bundle Branch Block (LBBB), Right Bundle Branch Block (RBBB) and Intra Ventricular Conduction Defects (IVCD). Single and dual chamber pacing of the right atrium and/or the right ventricle can be counterproductive in such cases, depending on the defective conduction pathway and the location of the pace/sense electrodes.

A number of proposals have been advanced for providing pacing therapies to alleviate theses conditions and restore synchronous depolarization of right and left, upper and lower, heart chambers. The proposals appearing in U.S. Pat. Nos. 3,937,266, 4,088,140, 4,548,203, 4,458,677 and 4,332,259 are summarized in U.S. Pat. Nos. 4,928,688 and 5,674,259, all incorporated herein by reference. The advantages of providing sensing at pace/sense electrodes located in both the right and left heart chambers are addressed in the '688 and '259 patents, as well as in U.S. Pat. Nos. 4,354,497, 5,174,289, 5,267,560, 5,514,161, 5,584,867, also all incorporated herein by reference. Typically, the right atrium is paced at expiration of an A-A escape interval, and the left atrium is simultaneously paced or synchronously paced after a short delay time. Similarly, the right ventricle is paced at expiration of a V-V escape interval, and the left ventricle is simultaneously paced or synchronously paced after a short delay. Some of these patents propose limited forms of DDD pacing having "bi-ventricular" or "bi-atrial" demand or triggered pacing functions. In all cases, a pacing pulse delivered at the end of the escape internal or AV delay (a "paced event") triggers the simultaneous or slightly delayed delivery of the pacing pulse to the other heart chamber. They do not propose pacing a right or left heart chamber at the end of the escape interval or AV delay and then inhibiting pacing in the other of the right or left heart chamber if a conducted depolarization is detected in that other heart chamber within a physiologic time related to the location of the pace/sense electrodes.

In the '259 patent, a combined epicardial IPG and electrode array are proposed for fitting about the apical region of the heart and providing a VVI pacing function providing for substantially simultaneous depolarization of both ventricles through selected ones of the pace/sense electrodes on time out of a V-V escape interval. It is not clear what occurs if an R-wave is sensed at one of the left or right ventricular pace/sense electrodes within the V-V escape interval.

In the '688 patent, two- or three-chamber pacing systems are disclosed wherein a programmable synchronization time window of about 5–10 msec duration is started on the sensing of an R-wave or a P-wave at pace/sense electrodes in one of the ventricles or atria before the expiration of a V-V or an A-A escape interval, respectively. The delivery of the pacing pulse in the other atrium or ventricle is inhibited if a P-wave or an R-wave is sensed at the pace/sense electrode site in that chamber within the synchronization time window in atrial or ventricular pace/sense electrodes if the V-V escape interval times out without sensing a P-wave or an R-wave at either pace/sense electrode site. In a DDD pacemaker context, an atrial pace/sense electrode, sense amplifier and pace output circuit and a pair of ventricular pace/sense electrodes, sense amplifiers and pace output circuits are provided. The AV delay timer is started when a P-wave is sensed, and ventricular pacing pulses are preferably supplied simultaneously to the two ventricular pace/sense electrodes if an R-wave is not sensed by either ventricular sense amplifier before the AV delay times out.

A double atrial, triple chamber pacing system is described in the '161 and '867 patents. Such a pacing system is used for treating dysfunctional atrial conduction using a programmable DDD pacemaker for pacing both atria simultaneously when an atrial sensed event is detected from either chamber or at the expiration of a V-A escape interval. The IPG includes atrial sense amplifiers coupled to atrial pace/sense electrodes positioned with respect to electrode sites in or adjacent the right and left atria and a ventricular sense amplifier coupled to ventricular pace/sense electrodes located in or on the right ventricle. In the '161 patent, ventricular pacing pulses are applied to the ventricular pace/sense electrodes at the end of an AV delay timed from the atrial paced events unless the sensed atrial rate exceeds a rate limit. In the '867 patent, a fall back mode is commenced to limit the ventricular pacing rate if the sensed P-wave are deemed "premature". Clinical experience in use of double atrial, three chamber, pacing systems appears in abstracts by Daubert et al., including "Permanent Dual Atrium Pacing in Major Intratrial Conduction Blocks: A Four Years Experience" appearing in PACE (Vol.16, Part II, NASPE Abstract 141, p. 885, April 1993). In these systems, atrial pacing pulses are delivered simultaneously in a triggered mode to both atria that is wasteful of electrical energy and fails to maintain a physiologic delay between the evoked depolarizations of the atria.

Further clinical experience with two, three and four heart chamber pacing is also reported by Daubert et al. in "Permanent Left Ventricular Pacing With Transvenous Leads Inserted Into The Coronary Veins" appearing in PACE (Vol. 21, Part II, pp. 239–245, January 1998). In the two heart chamber context, there is disclosed a method of implanting conventional DDDR IPGs with the atrial pace/sense terminals coupled to a left ventricular lead having pace/sense electrodes located in relation to the left ventricle. The ventricular pace/sense terminals were coupled to right ventricular leads having pace/sense electrodes located in relation to the right ventricle. The IPG was programmed to operate in the WIR mode with short AV delays, e.g. 30 ms, for timing delivery of a pacing pulse to the right ventricle when an R-wave was first sensed in or a pacing pulse was delivered to the left ventricle at the end of the programmed V-A escape interval. In this bi-ventricular pacing system, ventricular pacing pulses were not delivered in a triggered mode to both ventricles, but only the conduction delay from the left ventricle to the right ventricle could be programmed.

Also disclosed is the use of a double ventricular, triple chamber pacing system in the above article using DDDR IPGs having the atrial terminals coupled with the atrial pacing lead and the ventricular terminals coupled through an adaptor to two ventricular pacing leads. The pace/sense electrodes of the atrial pacing lead were implanted apparently in relation to the right atrium and the pace/sense electrodes of the ventricular pacing leads were implanted in relation to the right and left ventricles. The DDDR IPG was programmed in the DDDR mode to provide simultaneous pacing of the right and left ventricles at the end of an A-V delay timed from an atrial paced event at the expiration of the V-A pacing escape interval or an atrial sensed event occurring during the V-A escape interval. In this system, the simultaneous delivery of ventricular pacing pulses to both ventricles is wasteful of electrical energy and fails to maintain a physiologic delay between the evoked depolarizations of the ventricles.

A four chamber DDD pacing system providing right and left chamber pacing and sensing is described in the above article, and in an article by Cazeau et al., entitled "Four Chamber Pacing in Dilated Cardiomyopathy" appearing in PACE (Vol. 17, Part II, pp. 1974–1979, November 1994). In these and other four chamber systems, right and left atrial leads are coupled "in series" through a bifurcated bipolar adaptor with atrial pace/sense connector block terminals, and right and left ventricular leads are coupled "in series" through a bifurcated bipolar adaptor with ventricular pace/sense connector block terminals. Right atrial and right ventricular leads are connected to the cathode ports, while left atrial and left ventricular leads are connected to the anode ports of each bipolar bifurcated adaptor. The IPG is programmed in the DDD mode and in a bipolar pacing mode with a common AV delay that is connected by the delivery of atrial pacing pulses. The earliest right or left atrial sensed event (i.e., the P-wave) within a V-A escape interval or the expiration of the V-A escape interval triggers delivery of atrial pacing pulses to both of the pace/sense electrodes in both atrial chambers through the series connected, right and left atrial leads. It appears that the sensing "in series" of either a right or left ventricular R-wave across the right and left pace/sense electrode during the AV delay terminates the AV delay and triggers delivery of ventricular pace pulses across the right and left pace/sense electrode pair. In this pacing system, both atrial and ventricular pacing pulses are delivered to both atria and both ventricles on the sensing the P-wave and on the sensing R-wave, respectively, which is wasteful of electrical energy. Furthermore, the resulting simultaneous depolarization of the right and left atria or the right and left ventricles in not physiologically beneficial in many instances.

In these approaches, the atrial and/or ventricular pace/sense electrodes are located in a variety of locations and manner with respect to the right and left atria and/or the right and left ventricles. In the '688 patent, one ventriclar pace/sense electrode is located at the distal end of an endocardial lead introduced deeply into the great vein extending from the coronary sinus to place it adjacent to the left ventricle. It is also known that pace/sense electrode of an endocardial lead can be placed closer to the entrance to the coronary sinus and adjacent the left atrium. Such an approach is shown in the above referenced Cazeau et al. article and in an abstract by Daubert et al., "Renewal of Permanent Left Atrial Pacing via the Coronary Sinus", appearing in *PACE* (Vol. 15, Part II, NASPE Abstract 255, p. 572, April 1992), also incorporated herein by reference. Epicardial screw-in, pace/sense electrodes can also be placed epicardially on the right and left ventricles because the myocardial walls are thick enough to not be perforated in the process as also shown in the above referenced Cazeau article. In addition, a bi-ventricular pacemaker is proposed in the above-incorporated '259 patent having an array of ventricular pace/sense electrodes fitting about the apex of the heart to provide a plurality of usable epicardial pacing and/or sensing electrode sites about the apical region of the heart.

Additionally, "Coronary Sinus Pacing Prevents Induction of Atrial Fibrillation," by Papageorgiou et al., proposes a simultaneous high right atrial and coronary sinus pacing to prevent the induction of atrial fibrillation. That is, Papageorgiou proposes that distal coronary sinus pacing suppresses the propensity of high right atrial extra stimulus to induce atrial fibrillation by limiting their prematurity at the posterior triangle of Koch, while not allowing local conduction delay and local reentry to occur.

Furthermore, in "Multiple Channel, Sequential, Cardiac Pacing Systems," Struble et al. discloses an invention directed to providing symmetrically operating left and right heart chamber pacing systems. The pacing systems described in Struble overcome the problems and limitations, disclosed and described above, and provide a great deal of flexibility in tailoring the delivered pacing therapy to needs of the individual patient's heart.

Finally, in the Diva Functional Product Description, Regarding PVC synchronous atrial stimulation, a Vitatron device allows for PVC synchronous pacing. That is, when the mode of the pacing system is programmed to 'On,' the PVC synchronous atrial pacing feature paces the atrium of the patient's heart within 20 ms after recording a single PVC event. Furthermore, no atrial pacing function is released from the pacing system within a predetermined period of time from the last event, and the PVC synchronous atrial pacing feature is limited to the first PVC in a row of PVCs.

As discussed above, the most pertinent prior art patents are shown in the following table:

TABLE 1

| Prior Art Patents. | | |
|---|---|---|
| Patent No. | Date | Inventor(s) |
| 3,937,266 | 02-10-76 | Cordone et al. |
| 4,088,140 | 05-09-78 | Rockland et al. |
| 4,332,259 | 06-01-82 | McCorkle, Jr. |
| 4,354,497 | 10-19-82 | Kahn |
| 4,458,677 | 07-10-84 | McCorkle, Jr. |
| 4,548,203 | 10-22-85 | Tracker, Jr. et al. |
| 4,928,688 | 05-29-90 | Mower |
| 5,174,289 | 12-29-92 | Cohen |
| 5,267,560 | 12-07-93 | Cohen |
| 5,514,161 | 05-07-96 | Limousin |
| 5,584,867 | 12-17-96 | Limousin et al. |
| 5,674,259 | 10-07-97 | Gray |

All the patents listed in Table 1 are hereby incorporated by reference herein in their respective entireties. As those of ordinary skill in the art will appreciate readily upon reading the Summary of the Invention, the Detailed Description of the Preferred Embodiments and the Claims set forth below, many of the devices and methods disclosed in the patents of Table 1 may be modified advantageously by using the teachings of the present invention.

SUMMARY OF THE INVENTION

The present invention is therefore directed to providing a method and system for instantaneously stimulating the contraction of an atrium of a mammalian heart. Such a system of the present invention overcomes the problems, disadvantages and limitations of the prior art described above, and provides a more efficient and accurate means of immediately contractually stimulating the left atrium of a mammalian heart.

The present invention has certain objects. That is, various embodiments of the present invention provide solutions to one or more problems existing in the prior art respecting the instantaneous stimulation of the contraction of an atrium of a mammalian heart. Those problems include, without limitation: a time delay between the recording of a premature atrial contraction in a first atrium and the stimulation in a second atrium, the recording of a premature atrial contraction in the right atrium and the stimulation of the left atrium upon the above-noted recording.

In comparison to known techniques for stimulating the contraction of an atrium of a mammalian heart, various embodiments of the present invention may provide one or more of the following advantages: the instantaneous stimulation of a second atrium of a mammalian heart, the recording of a premature atrial contraction in the right atrium and the stimulation of the left atrium upon the above-noted recording.

Some of the embodiments of the present invention include one or more of the following features: an implantable medical device including at least one sensing lead, at least one pacing lead, a microprocessor and an input/output circuit including a digital controller/timer circuit, an output amplifier, a sense amplifier, a peak sense and threshold measurement device, a comparator and an electrogram amplifier.

Furthermore, in accordance with the present invention, an embodiment providing for a method and system of stimulating a mammalian heart is provided. This embodiment provides a processor contained within an implantable medical device monitors the intervals between successive beats of the mammalian heart. The processor then measures the interval times and furthermore calculates an average interval time. When one of the interval times is substantially less than the average interval time, the processor will classify that particular interval as containing a premature atrial contraction. When a premature atrial contraction has been detected, the processor will transmit a signal to the left atrium, instructing the left atrium to contract. As a result, the left atrium contracts immediately after the detection of the premature atrial contraction, thereby negating and preventing the start of an atrial tachyarrhythmia.

Therefore, the algorithm of the present invention enables the implantable medical device to trigger the stimulation of the right atrium in response to spontaneous activity sensed by the electrode in the coronary sinus. In this way, it is possible to synchronize the left and right atria in reaction to any spontaneous activity that is sensed. As a result, this mode of pacing may therefore prevent the start of atrial tachyarrhythmia.

BRIEF DESCRIPTION OF THE DRAWINGS

The above, and other objects, advantages and features of the present invention will be more readily understood from the following detailed description of the preferred embodiments thereof, when considered in conjunction with the drawings, in which like reference numerals indicate identical structures throughout the several views, and wherein.

DETAILED DESCRIPTION OF THE PRESENTLY PREFERRED EMBODIMENTS

Figure 1:
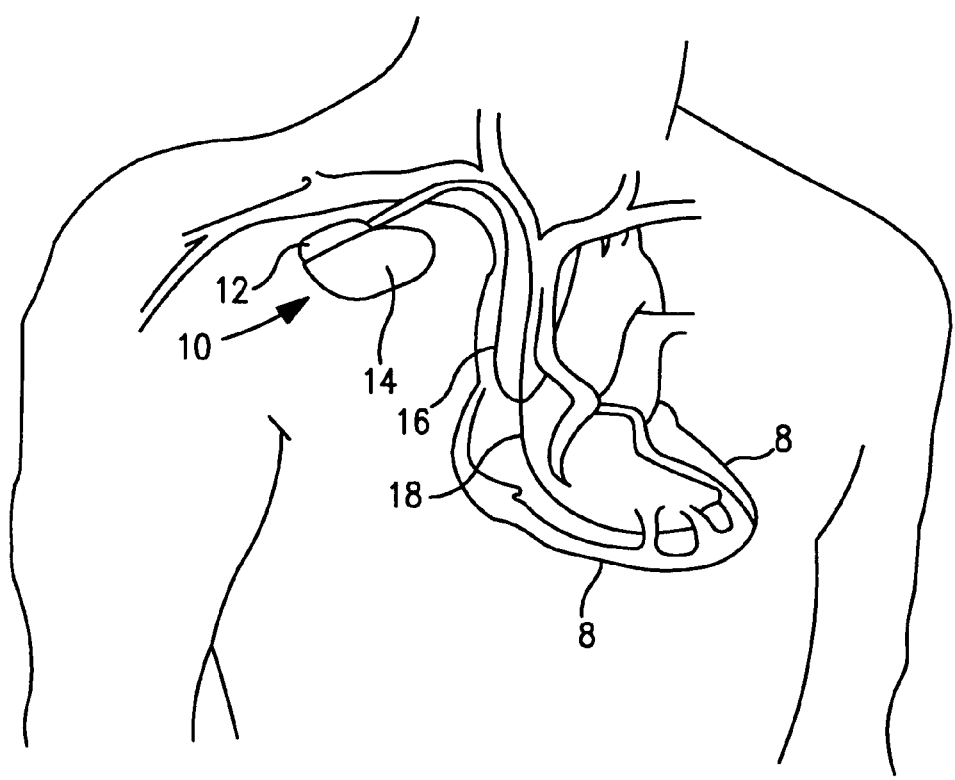
FIG. 1 is a schematic view of an implantable medical device, made in accordance with the present invention.

FIG. 1 is a simplified schematic view of one embodiment of implantable medical device ("IMD") 10 of the present invention. The IMD 10 shown in FIG. 1 is a pacemaker comprising at least one of pacing and sensing leads 16 and 18 attached to hermetically sealed enclosure 14 and implanted near human or mammalian heart 8. Pacing and sensing leads 16 and 18 sense electrical signals attendant to the depolarization and re-polarization of the heart 8, and further provide pacing pulses for causing depolarization of cardiac tissue in the vicinity of the distal ends thereof. Leads 16 and 18 may have unipolar or bipolar electrodes disposed thereon, as is well known in the art. Examples of IMD 10 include implantable cardiac pacemakers disclosed in U.S. Pat. No. 5,158,078 to Bennett et al., U.S. Pat. No. 5,312,453 to Shelton et al. or U.S. Pat. No. 5,144,949 to Olson, all of which are hereby incorporated by reference, each in their respective entireties.

Figure 2:
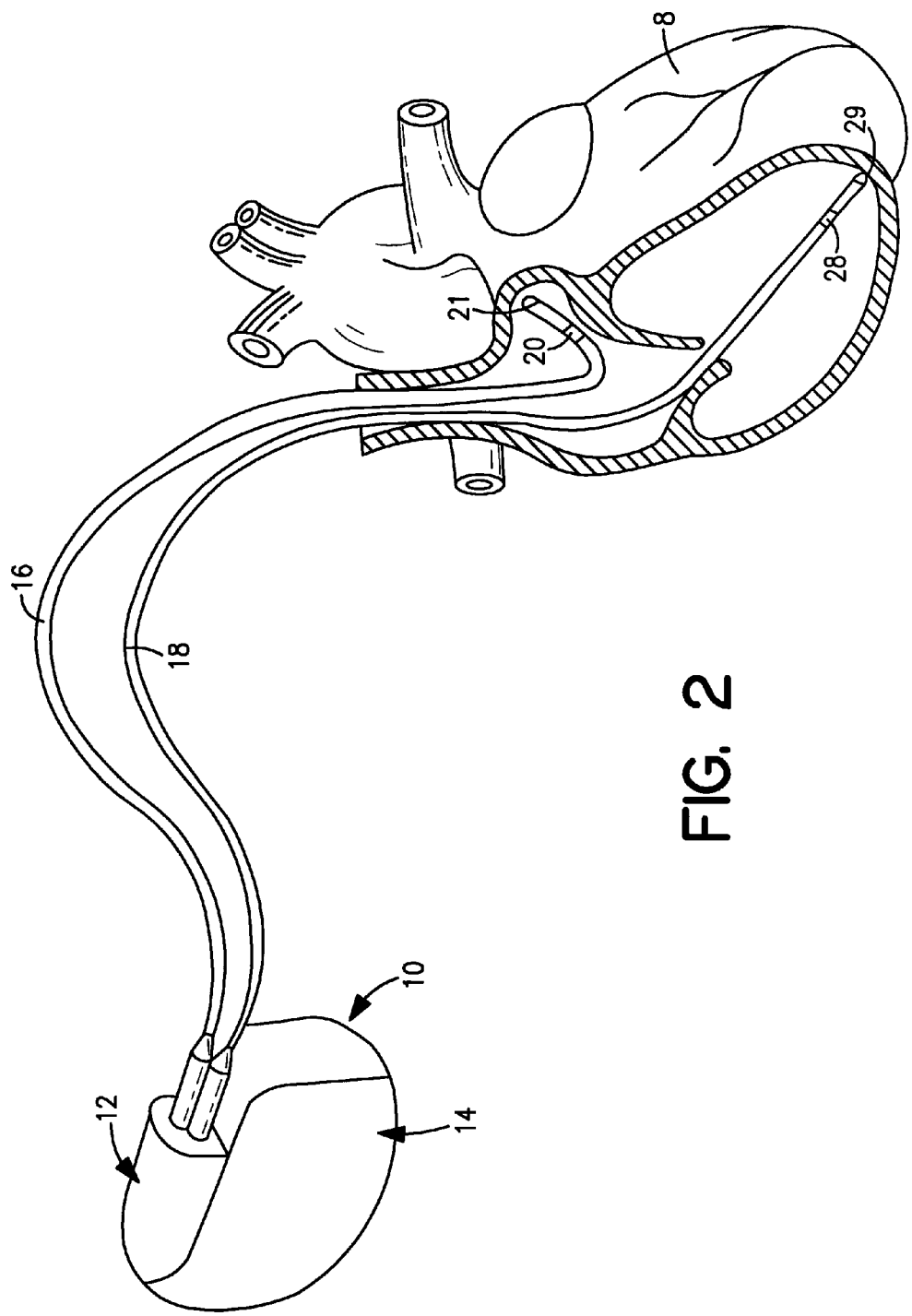
FIG. 2 is another view of the implantable medical device of FIG. 1, made in accordance with the present invention.

FIG. 2 shows connector module 12 and hermetically sealed enclosure 14 of IMD 10 located in and near human or mammalian heart 8. Atrial and ventricular pacing leads 16 and 18 extend from connector header module 12 to the right atrium and ventricle, respectively, of heart 8. Atrial electrodes 20 and 21 disposed at the distal end of atrial pacing lead 16 are located in the right atrium. Ventricular electrodes 28 and 29 at the distal end of ventricular pacing lead 18 are located in the right ventricle.

Figure 3:
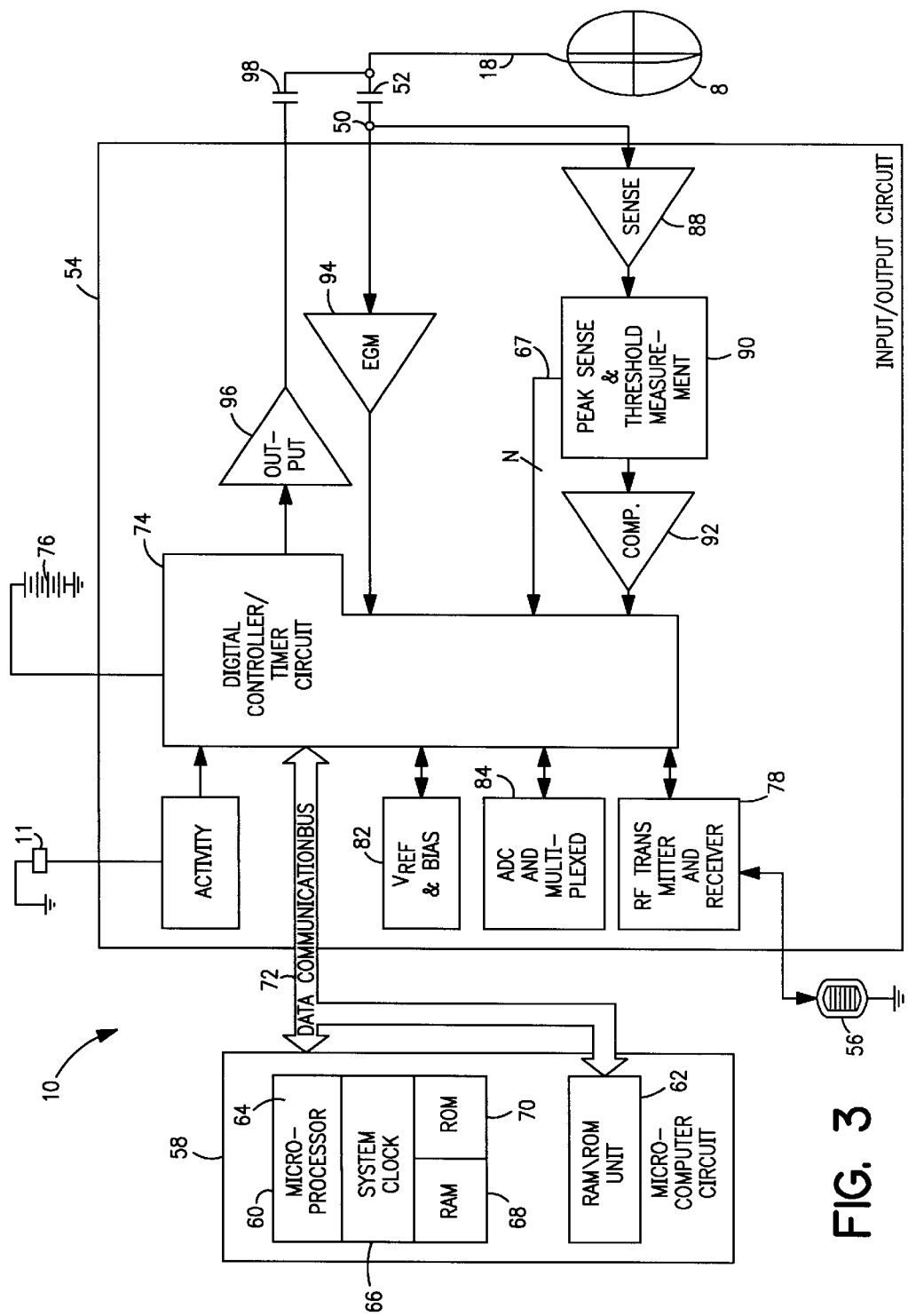
FIG. 3 shows a block diagram illustrating the components of the implantable medical device of FIG. 1, made in accordance with the present invention.

FIG. 3 shows a block diagram illustrating the constituent components of IMD 10 in accordance with one embodiment of the present invention, where IMD 10 is a pacemaker having a microprocessor-based architecture. IMD 10 is shown as including activity sensor or accelerometer 11, which is preferably a piezoceramic accelerometer bonded to a hybrid circuit located inside enclosure 14. Activity sensor 11 typically (although not necessarily) provides a sensor output that varies as a function of a measured parameter relating to a patient's metabolic requirements. For the sake of convenience, IMD 10 in FIG. 3 is shown with lead 18 only connected thereto; similar circuitry and connections not explicitly shown in FIG. 3 apply to lead 16.

IMD 10 in FIG. 3 is most preferably programmable by means of an external programming unit (not shown in the FIGS.). One such programmer is the commercially available Medtronic Model 9790 programmer, which is microprocessor-based and provides a series of encoded signals to IMD 10, typically through a programming head which transmits or telemeters radio-frequency (RF) encoded signals to IMD 10. Such a telemetry system is described in U.S. Pat. No. 5,312,453 to Wyborny et al., hereby incorporated by reference in its entirety. The programming methodology disclosed in the '453 patent is identified herein for illustrative purposes only. Any of a number of suitable programming and telemetry methodologies known in the art may be employed so long as the desired information is transmitted to and from the pacemaker.

As shown in FIG. 3, lead 18 is coupled to node 50 in IMD 10 through input capacitor 52. Activity sensor or accelerometer 11 is most preferably attached to a hybrid circuit located inside hermetically sealed enclosure 14 of IMD 10. The output signal provided by activity sensor 11 is coupled to input/output circuit 54. Input/output circuit 54 contains analog circuits for interfacing to heart 8, activity sensor 11, antenna 56 and circuits for the application of stimulating pulses to heart 8. The rate of heart 8 is controlled by software-implemented algorithms stored microcomputer circuit 58.

Microcomputer circuit 58 preferably comprises on-board circuit 60 and off-board circuit 62. Circuit 58 may correspond to a microcomputer circuit disclosed in U.S. Pat. No. 5,312,453 to Shelton et al., hereby incorporated by reference in its entirety. On-board circuit 60 preferably includes microprocessor 64, system clock circuit 66 and on-board RAM 68 and ROM 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 are powered by an appropriate implantable battery power source 76 in accordance with common practice in the art. For the sake of clarity, the coupling of battery power to the various components of IMD 10 is not shown in the FIGS. Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,566,063, issued to Thompson et al. and hereby incorporated by reference in its entirety, or to that disclosed in the above-referenced '453 patent. It is generally preferred that the particular programming and telemetry scheme selected permit the entry and storage of cardiac rate-response parameters. The specific embodiments of antenna 56, input/output circuit 54 and telemetry unit 78 presented herein are shown for illustrative purposes only, and are not intended to limit the scope of the present invention.

Continuing to refer to FIG. 3, $V_{REF}$ and Bias circuit 82 most preferably generates stable voltage reference and bias currents for analog circuits included in input/output circuit 54. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of IMD 10 are coupled by data communication bus 72 to digital controller/timer circuit 74, where digital timers and counters establish the overall escape interval of the IMD 10 as well as various refractory, blanking and other timing windows for controlling the operation of peripheral components disposed within input/output circuit 54.

Digital controller/timer circuit 74 is preferably coupled to sensing circuitry, including sense amplifier 88, peak sense and threshold measurement unit 90 and comparator/threshold detector 92. Circuit 74 is further preferably coupled to electrogram (EGM) amplifier 94 for receiving amplified and processed signals sensed by lead 18. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 67 to digital controller/timer circuit 74. An amplified sense amplifier signal is then provided to comparator/threshold detector 92. By way of example, sense amplifier 88 may correspond to that disclosed in U.S. Pat. No. 4,379,459 to Stein, hereby incorporated by reference in its entirety.

The electrogram signal provided by EGM amplifier 94 is employed when IMD 10 is being interrogated by an external programmer to transmit a representation of a cardiac analog electrogram. See, for example, U.S. Pat. No. 4,556,063 to Thompson et al., hereby incorporated by reference herein in its entirety. Output pulse generator 96 provides pacing stimuli to patient's heart 8 through coupling capacitor 98 in response to a pacing trigger signal provided by digital controller/timer circuit 74 each time the escape interval times out, an externally transmitted pacing command is received or in response to other stored commands as is well known in the pacing art. By way of example, output amplifier 96 may correspond generally to an output amplifier disclosed in U.S. Pat. No. 4,476,868 to Thompson, hereby incorporated by reference in its entirety.

The specific embodiments of input amplifier 88, output amplifier 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 8.

In some preferred embodiments of the present invention, IMD 10 may operate in various non-rate-responsive modes, including, but not limited to, DDD, DDI, VVI, VOO and WT modes. In other preferred embodiments of the present invention, IMD 10 may operate in various rate-responsive, including, but not limited to, DDDR, DDIR, VVIR, VOOR and VVTR modes. Some embodiments of the present invention are capable of operating in both non-rate-responsive and rate responsive modes. Moreover, in various embodiments of the present invention IMD 10 may be programmably configured to operate so that it varies the rate at which it delivers stimulating pulses to heart 8 only in response to one or more selected sensor outputs being generated. Numerous pacemaker features and functions not explicitly mentioned herein may be incorporated into IMD 10 while remaining within the scope of the present invention.

The present invention is not limited in scope to single-sensor or dual-sensor pacemakers, and is further not limited to IMD's comprising activity or pressure sensors only. Nor is the present invention limited in scope to single-chamber pacemakers, single-chamber leads for pacemakers or single-sensor or dual-sensor leads for pacemakers. Thus, various embodiments of the present invention may be practiced in conjunction with more than two leads or with multiple-chamber pacemakers, for example. At least some embodiments of the present invention may be applied equally well in the contexts of single-, dual-, triple- or quadruple- chamber pacemakers or other types of IMD's. See, for example, U.S. Pat. No. 5,800,465 to Thompson et al., hereby incorporated by reference herein in its entirety, as are all U.S. Patents referenced therein.

IMD 10 may also be a pacemaker-cardioverter-defibrillator ("PCD") corresponding to any of numerous commercially available implantable PCD's. Various embodiments of the present invention may be practiced in conjunction with PCD's such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless and U.S. Pat. No. 4,821,723 to Baker et al., all of which are hereby incorporated by reference, each in their respective entireties.

Figure 4:
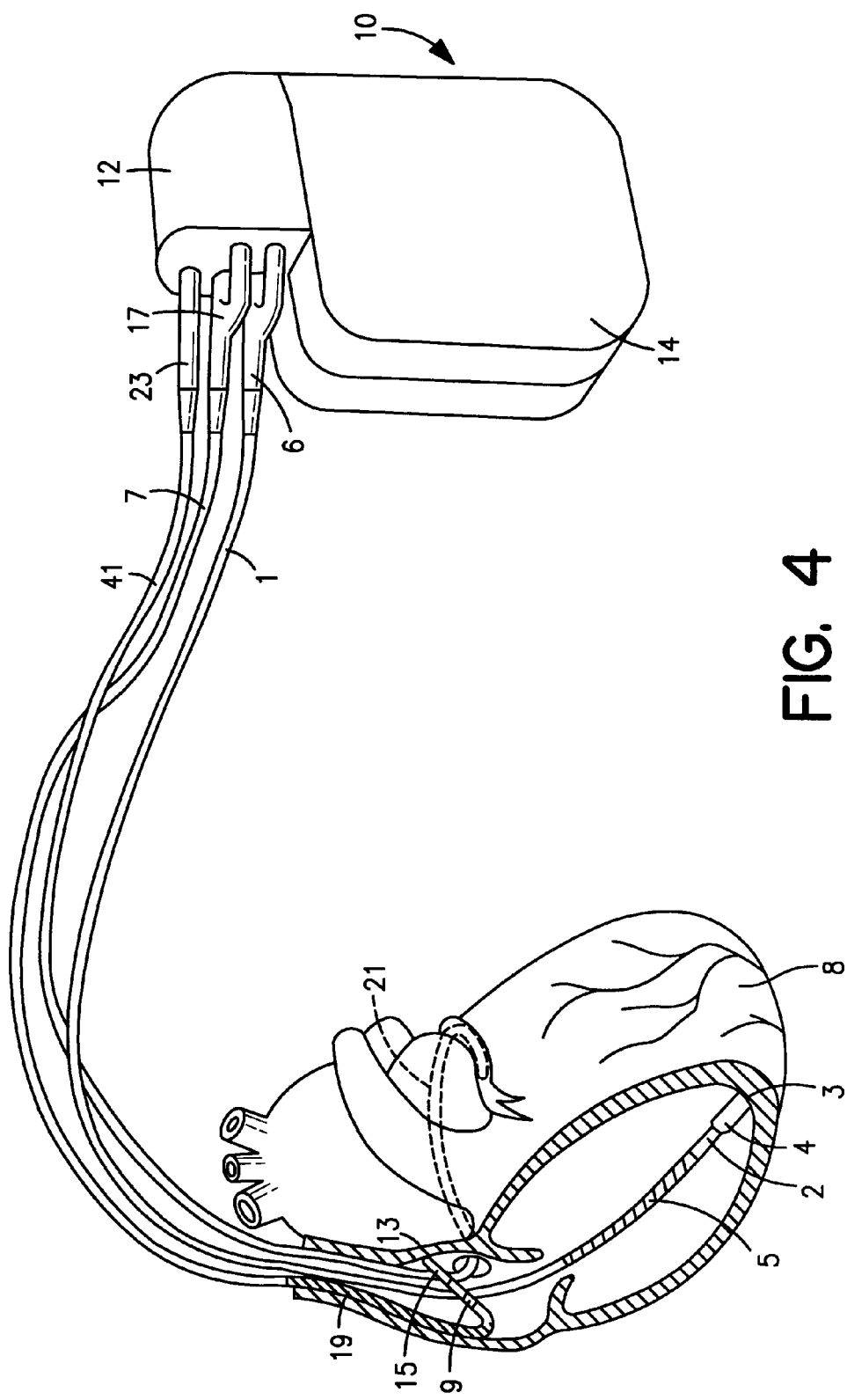
FIG. 4 illustrates another embodiment of the implantable medical device of FIG. 1, made in accordance with the present invention.
Figure 5:
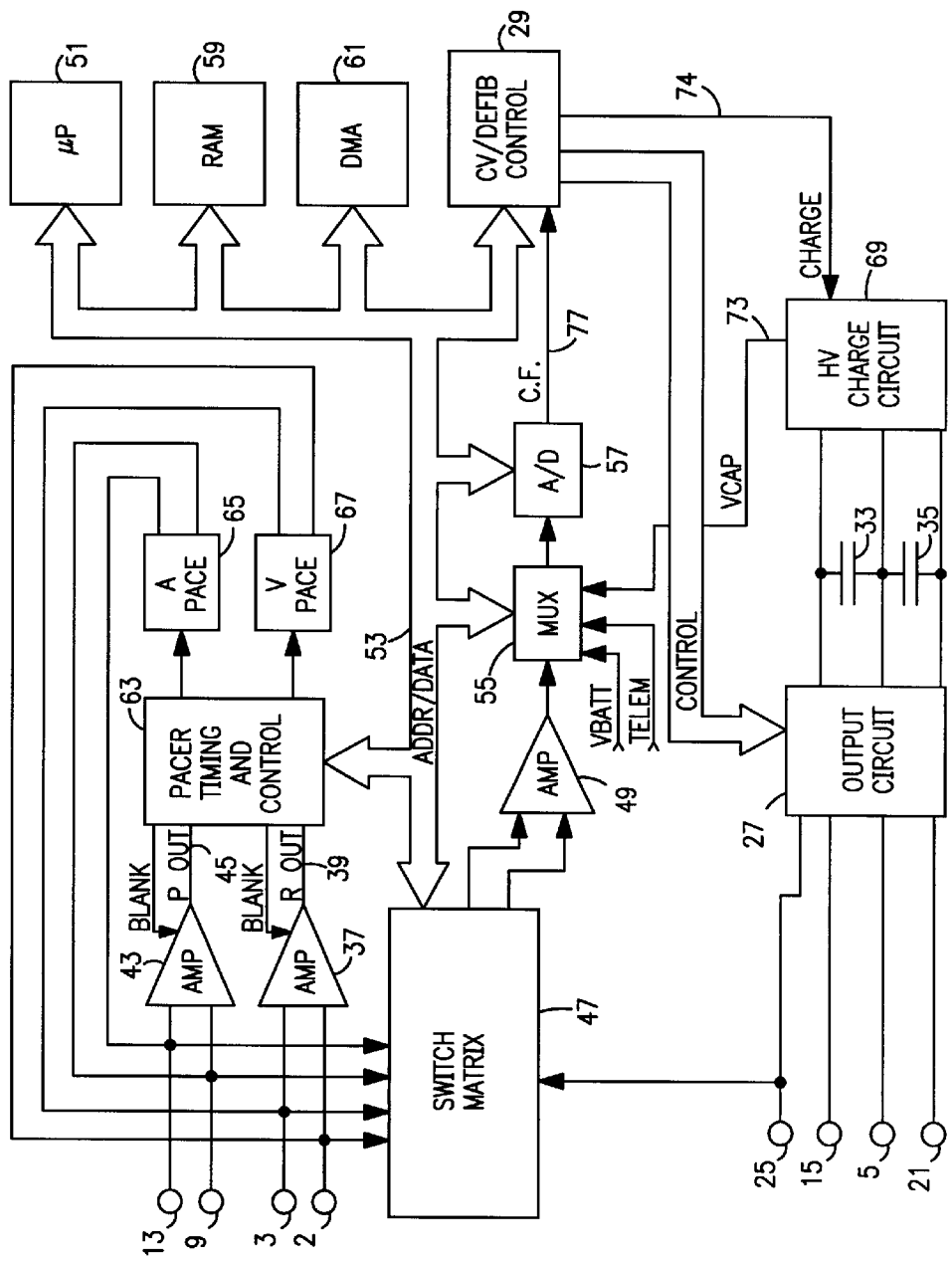
FIG. 5 illustrates a block diagram of the embodiment of FIG. 4, made in accordance with the present invention.

FIGS. 4 and 5 illustrate one embodiment of IMD 10 and a corresponding lead set of the present invention, where IMD 10 is a PCD. In FIG. 4, the ventricular lead takes the form of leads disclosed in the '838 and '430 patents, and includes an elongated insulative lead body 1 carrying three concentric coiled conductors separated from one another by tubular insulative sheaths. Located adjacent the distal end of lead 1 are ring electrode 2, extendable helix electrode 3 mounted retractably within insulative electrode head 4 and elongated coil electrode 5. Each of the electrodes is coupled to one of the coiled conductors within lead body 1. Electrodes 2 and 3 are employed for cardiac pacing and for sensing ventricular depolarizations. At the proximal end of the lead is bifurcated connector 6, which carries three electrical connectors, each coupled to one of the coiled conductors. Defibrillation electrode 5 may be fabricated from platinum, platinum alloy or other materials known to be usable in implantable defibrillation electrodes and may be about 5 cm in length.

The atrial/SVC lead shown in FIG. 4 includes elongated insulative lead body 7 carrying three concentric coiled conductors separated from one another by tubular insulative sheaths corresponding to the structure of the ventricular lead. Located adjacent the J-shaped distal end of the lead are ring electrode 9 and extendable helix electrode 13 mounted retractably within an insulative electrode head 15. Each of the electrodes is coupled to one of the coiled conductors within lead body 7. Electrodes 13 and 9 are employed for atrial pacing and for sensing atrial depolarizations. Elongated coil electrode 19 is provided proximal to electrode 9 and coupled to the third conductor within lead body 7. Electrode 19 preferably is 10 cm in length or greater and is configured to extend from the SVC toward the tricuspid valve. In one embodiment of the present invention, approximately 5 cm of the right atrium/SVC electrode is located in the right atrium with the remaining 5 cm located in the SVC. At the proximal end of the lead is bifurcated connector 17, which carries three electrical connectors, each coupled to one of the coiled conductors.

The coronary sinus lead shown in FIG. 4 assumes the form of a coronary sinus lead disclosed in the above cited '838 patent, and includes elongated insulative lead body 41 carrying one coiled conductor coupled to an elongated coiled defibrillation electrode 21. Electrode 21, illustrated in broken outline in FIG. 4, is located within the coronary sinus and the great vein of the heart. At the proximal end of the lead is connector plug 23 carrying an electrical connector coupled to the coiled conductor. The coronary sinus/great vein electrode 41 may be about 5 cm in length.

Implantable PCD 10 is shown in FIG. 4 in combination with leads 1, 7 and 41, and lead connector assemblies 23, 17 and 6 inserted into connector block 12. Optionally, insulation of the outward facing portion of housing 14 of PCD 10 may be provided using a plastic coating such as parylene or silicone rubber, as is employed in some unipolar cardiac pacemakers. The outward facing portion, however, may be left uninsulated or some other division between insulated and uninsulated portions may be employed. The uninsulated portion of housing 14 serves as a subcutaneous defibrillation electrode to defibrillate either the atria or ventricles. Lead configurations other that those shown in FIG. 4 may be practiced in conjunction with the present invention, such as those shown in U.S. Pat. No. 5,690,686 to Min et al., hereby incorporated by reference in its entirety.

FIG. 5 is a functional schematic diagram of one embodiment of implantable PCD 10 of the present invention. This diagram should be taken as exemplary of the type of device in which various embodiments of the present invention may be embodied, and not as limiting, as it is believed that the invention may be practiced in a wide variety of device implementations, including cardioverter and defibrillators which do not provide anti-tachycardia pacing therapies.

PCD 10 is provided with an electrode system. If the electrode configuration of FIG. 4 is employed, the correspondence to the illustrated electrodes is as follows. Electrode 25 in FIG. 5 includes the uninsulated portion of the housing of PCD 10. Electrodes 25, 15, 21 and 5 are coupled to high voltage output circuit 27, which includes high voltage switches controlled by CV/defib control logic 29 via control bus 31. Switches disposed within circuit 27 determine which electrodes are employed and which electrodes are coupled to the positive and negative terminals of the capacitor bank (which includes capacitors 33 and 35) during delivery of defibrillation pulses.

Electrodes 2 and 3 are located on or in the ventricle and are coupled to the R-wave amplifier 37, which preferably takes the form of an automatic gain controlled amplifier providing an adjustable sensing threshold as a function of the measured R-wave amplitude. A signal is generated on R-out line 39 whenever the signal sensed between electrodes 2 and 3 exceeds the present sensing threshold.

Electrodes 9 and 13 are located on or in the atrium and are coupled to the P-wave amplifier 43, which preferably also takes the form of an automatic gain controlled amplifier providing an adjustable sensing threshold as a function of the measured P-wave amplitude. A signal is generated on P-out line 45 whenever the signal sensed between electrodes 9 and 13 exceeds the present sensing threshold. The general operation of R-wave and P-wave amplifiers 37 and 43 may correspond to that disclosed in U.S. Pat. No. 5,117,824, by Keimel et al., issued Jun. 2, 1992, for "An Apparatus for Monitoring Electrical Physiologic Signals," hereby incorporated by reference in its entirety.

Switch matrix 47 is used to select which of the available electrodes are coupled to wide band (0.5–200 Hz) amplifier 49 for use in digital signal analysis. Selection of electrodes is controlled by the microprocessor 51 via data/address bus 53, which selections may be varied as desired. Signals from the electrodes selected for coupling to bandpass amplifier 49 are provided to multiplexer 55, and thereafter converted to multi-bit digital signals by A/D converter 57, for storage in RAM 59 under control of direct memory access circuit 61. Microprocessor 51 may employ digital signal analysis techniques to characterize the digitized signals stored in RAM 59 to recognize and classify the patient's heart rhythm employing any of the numerous signal processing methodologies known to the art.

The remainder of the circuitry is dedicated to the provision of cardiac pacing, cardioversion and defibrillation therapies, and, for purposes of the present invention, may correspond to circuitry known to those skilled in the art. The following exemplary apparatus is disclosed for accomplishing pacing, cardioversion and defibrillation functions. Pacer timing/control circuitry 63 preferably includes programmable digital counters which control the basic time intervals associated with DDD, VVI, DVI, VDD, AAI, DDI and other modes of single and dual chamber pacing well known to the art. Circuitry 63 also preferably controls escape intervals associated with anti-tachyarrhythmia pacing in both the atrium and the ventricle, employing any anti-tachyarrhythmia pacing therapies known to the art.

Intervals defined by pacing circuitry 63 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 51, in response to stored data in memory 59 and are communicated to pacing circuitry 63 via address/data bus 53. Pacer circuitry 63 also determines the amplitude of the cardiac pacing pulses under control of microprocessor 51.

During pacing, escape interval counters within pacer timing/control circuitry 63 are reset upon sensing of R-waves and P-waves as indicated by a signals on lines 39 and 45, and in accordance with the selected mode of pacing on time-out trigger generation of pacing pulses by pacer output circuitry 65 and 67, which are coupled to electrodes 9, 13, 2 and 3. Escape interval counters are also reset on the generation of pacing pulses and thereby control the basic timing of cardiac pacing functions, including anti-tachyarrhythmia pacing. The durations of the intervals defined by escape interval timers are determined by microprocessor 51 via data/address bus 53. The value of the count present in the escape interval counters when reset by sensed R-waves and P-waves may be used to measure the durations of R-R intervals, P-P intervals, P-R intervals and R-P intervals, which measurements are stored in memory 59 and used to detect the presence of tachyarrhythmias.

Microprocessor 51 most preferably operates as an interrupt driven device, and is responsive to interrupts from pacer timing/control circuitry 63 corresponding to the occurrence sensed P-waves and R-waves and corresponding to the generation of cardiac pacing pulses. Those interrupts are provided via data/address bus 53. Any necessary mathematical calculations to be performed by microprocessor 51 and any updating of the values or intervals controlled by pacer timing/control circuitry 63 take place following such interrupts.

Detection of atrial or ventricular tachyarrhythmias, as employed in the present invention, may correspond to any of the various tachyarrhythmia detection algorithms presently known in the art. For example, the presence of an atrial or ventricular tachyarrhythmia may be confirmed by detecting a sustained series of short R-R or P-P intervals of an average rate indicative of tachyarrhythmia or an unbroken series of short R-R or P-P intervals. The suddenness of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann, U.S. Pat. No. 4,880,005, issued to Pless et al. and U.S. Pat. No. 4,830,006, issued to Haluska et al., all hereby incorporated by reference, each in their respective entirety. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10, 1986, *IEEE Computer Society Press*, pp. 167–170, also hereby incorporated by reference in its entirety. Atrial fibrillation detection methodologies are disclosed in published PCT Application Ser. No. US92/02829, Publication No. WO92/18198, by Adams et al., and in the article "Automatic Tachycardia Recognition", by Arzbaecher et al., published in *PACE*, May–June, 1984, pp. 541–547, both of which are hereby incorporated by reference in their entireties.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 51 into the pacer timing and control circuitry 63, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 4,726,380, issued to Vollmann et al. on Feb. 23, 1988 and U.S. Pat. No. 4,587,970, issued to Holley et al. on May 13, 1986, all of which are hereby incorporated by reference in their entireties, may also be employed.

In the event that the generation of a cardioversion or defibrillation pulse is required, microprocessor 51 may employ an escape interval counter to control timing of such cardioversion and defibrillation pulses, as well as the associated refractory periods. In response to the detection of atrial or ventricular fibrillation or tachyarrhythmia requiring a cardioversion pulse, microprocessor 51 activates cardioversion/defibrillation control circuitry 29, which initiates charging of the high voltage capacitors 33 and 35 via charging circuit 69, under the control of high voltage charging control line 71. The voltage on the high voltage capacitors is monitored via VCAP line 73, which is passed through multiplexer 55 and in response to reaching a predetermined value set by microprocessor 51, results in generation of a logic signal on Cap Full (CF) line 77 to terminate charging. Thereafter, timing of the delivery of the defibrillation or cardioversion pulse is controlled by pacer timing/control circuitry 63. Following delivery of the fibrillation or tachycardia therapy, microprocessor 51 returns the device to q cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al. and U.S. Pat. No. 4,316,472 to Mirowski et al., all of which are hereby incorporated by reference, each in its respective entirety. Any known cardioversion or defibrillation pulse control circuitry is believed to be usable in conjunction with various embodiments of the present invention, however. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., all of which are hereby incorporated by reference in their entireties, may also be employed.

Continuing to refer to FIG. 5, delivery of cardioversion or defibrillation pulses may be accomplished by output circuit 27 under the control of control circuitry 29 via control bus 31. Output circuit 27 determines whether a monophasic or biphasic pulse is delivered, the polarity of the electrodes and which electrodes are involved in delivery of the pulse. Output circuit 27 also includes high voltage switches which control whether electrodes are coupled together during delivery of the pulse. Alternatively, electrodes intended to be coupled together during the pulse may simply be permanently coupled to one another, either exterior to or within the interior of the device housing, and polarity may similarly be pre-set, as in current implantable defibrillators. An example of output circuitry for delivery of biphasic pulse regimens to multiple electrode systems may be found in U.S. Pat. No. 4,953,551, issued to Mehra, and in U.S. Pat. No. 4,727,877, both of which are hereby incorporated by reference in their entireties.

An example of circuitry which may be used to control delivery of monophasic pulses is disclosed in U.S. Pat. No. 5,163,427 to Keimel, also hereby incorporated by reference in its entirety. Output control circuitry similar to that disclosed in the '551 patent or in U.S. Pat. No. 4,800,883 to Winstrom, which is hereby incorporated by reference in its entirety, may also be used in conjunction with various embodiments of the present invention to deliver biphasic pulses.

Alternatively, IMD 10 may be an implantable nerve stimulator or muscle stimulator, such as that disclosed in U.S. Pat. No. 5,199,428 to Obel et al., U.S. Pat. No. 5,207,218 to Carpentier et al. or U.S. Pat. No. 5,330,507 to Schwartz, or an implantable monitoring device such as that disclosed in U.S. Pat. No. 5,331,966 issued to Bennet et al., all of which are hereby incorporated by reference, each in their respective entireties. The present invention is believed to find wide application to any form of implantable electrical device for use in conjunction with electrical leads.

As stated above, the IMD 10 of the present invention can perform a variety of functions. One function of the IMD 10 of the present invention may be to prevent atrial tachyarrhythmia. One of the possible intitators of an atrial tachyarrythmia may be a premature atrial contraction (PAC). In general, a PAC occurs when the interval between successive R-R or P-P intervals is much less than the average interval time between successive R-R or P-P intervals. A PAC may pose a number of problems to the patient. For example, when a PAC does not reset the sinusrhythm, the next sinuspulse may occur during a vulnerable period of the atrium, during which some, although not necessarily all, of the atrial tissue may be excitable. Essentially, resetting the sinusrhythm entails forcing a contraction in the atrium opposite the atrium in which the PAC was detected. Furthermore, it is well-known that the vulnerable period of the atrium occurs almost immediately after a PAC has occurred.

A dual-chamber pacemaker may be used in a bi-atrial pacing system, such as that used in an embodiment of the present invention, to alleviate the problems caused by unstable atrial arrythmias, such as, for example, atrial tachyarrythmia. One lead (such as, for example, the sensing lead 7 including electrodes 9, 13 in FIG. 4) is preferably placed in the right atrium of the mammalian heart 8. A second lead (such as, for example, a pacing lead 41 including electrode 21 in FIG. 4) is preferably placed in the coronary sinus (i.e., the left atrium). Alternatively, the sensing lead 7 may be placed in the left atrium, and the pacing lead 41 in the right. As a result, a sensed or paced event (preferably corresponding to a PAC) in the "sensed" atrium may trigger the immediate contractual stimulation of the "paced" atrium. The "AV-delay," or, in this case, the delay between the first and second atrial pacing signals, is preferably very short. The purpose for this short delay is to ensure the instantaneous contractual stimulation of the left atrium (i.e., the resetting of the sinusrhythm). Additionally, it should be noted that in such a pacing therapy, it would preferably be optimal to have the option to program the AV-delay to 0 ms (or, potentially, even a negative value) in order to obtain optimal synchrony between the atria and the ventricles on both the right and left sides of the heart 8.

Figure 6:
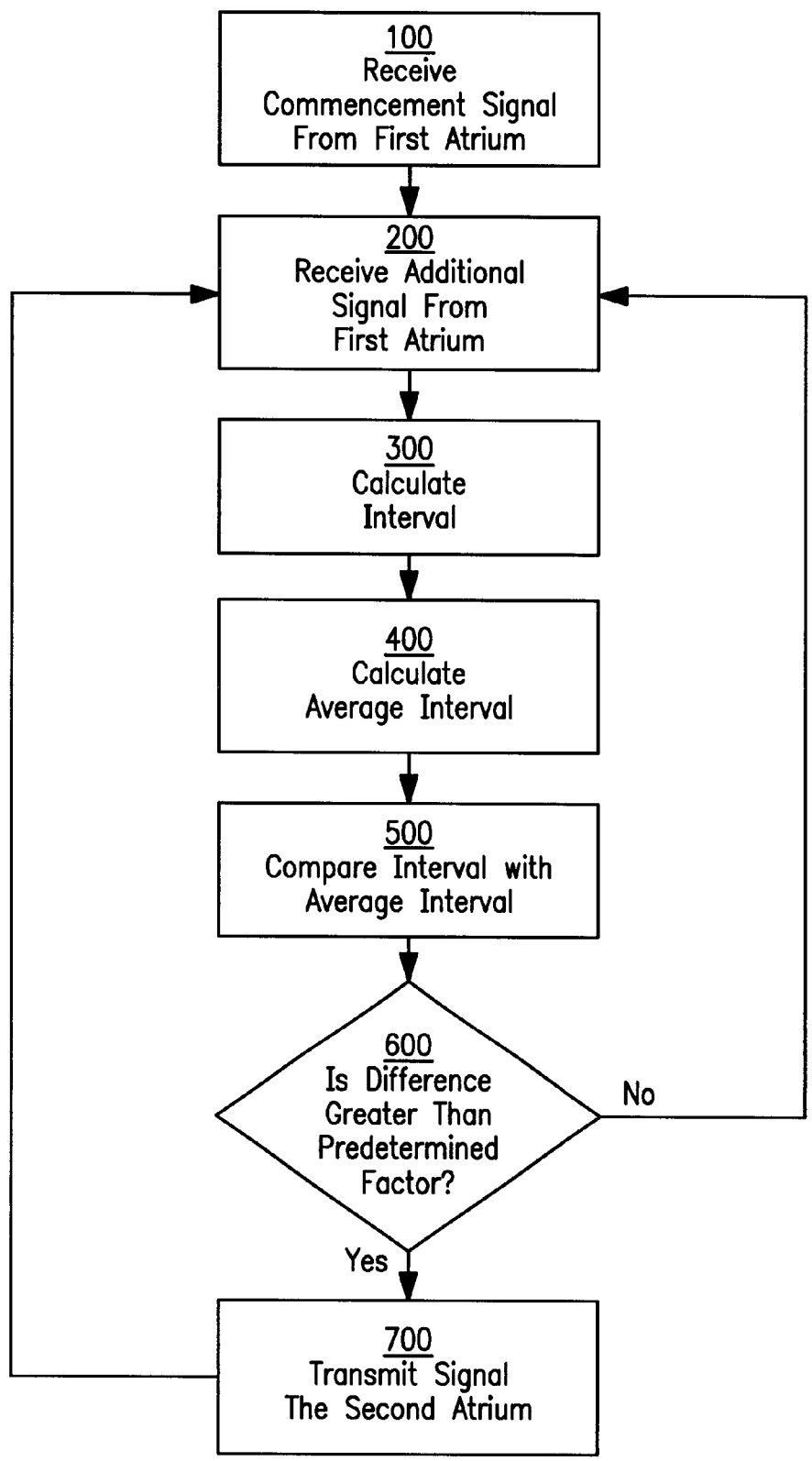
FIG. 6 illustrates a flow chart of a method for stimulating a mammalian heart, in accordance with the present invention.

FIG. 6 depicts a flow chart illustrating one embodiment of an algorithm for instantaneously stimulating the contraction of an atrium of a mammalian heart 8 after a PAC has been detected, in accordance with the present invention. In Blocks 100 and 200, the IMD 10 (or, more specifically, the microprocessor 64 within the IMD 10) begins to receive heartbeats from one atrium (the "sensed" atrium) of the mammalian heart 8. Preferably, the reception of the heartbeats may occur through the following method. First, the microprocessor 64 receives a commencement signal from one of the sensing leads 7 disposed in the sensed atrium. This is shown in Block 100. Second, in Block 200, the microprocessor 64 receives another signal from the sensing lead 7. Preferably, both of the signals received correspond to a heartbeat of the mammalian heart 8. Alternatively, the signals may correspond to other events of the mammalian heart 8 which may signify the start of a PAC.

In Block 300, the microprocessor 64, after receiving the signals, as described above, measures an interval. Preferably, the interval time is the time period elapsed between successive signals (which preferably correspond to R-R or P-P intervals). In Block 400, the microprocessor 64 then measures an average interval. Preferably, the average interval is measured according to known methods, and preferably consists of summing the individual intervals and dividing by the total number of intervals measured. It is preferable that the average interval be a moving average interval. Alternatively, the average interval may be an accumulating average interval.

In Block 500, the microprocessor 64 compares the interval measured in Block 300 with the average interval, as measured in Block 400. According to a preferred embodiment, the present invention, the microprocessor 64 compares the two intervals to determine whether the interval is substantially less than the average interval, thus indicating a PAC. A substantial difference between the interval and average interval occurs when the interval is less than the average interval by at least a predetermined factor. The predetermined factor preferably corresponds to the time required for the mammalian heart 8 to progress through, for example, 15 beats per minute (bpm). Alternatively, a predetermined factor different than 15 bpm may be used, such as, for example, 10 or 20 beats per minute.

In Block 600, if the difference between the interval and average interval is less than the predetermined factor (i.e., if a PAC is not detected), the microprocessor 64 continues to process the signals from the sensing lead. However, upon the detection of a PAC in the first atrium (i.e., in which case the difference between the interval and average interval is greater than the predetermined factor), the IMD 10 then immediately transmits a signal to the "paced" atrium (Block 700). That is, the microprocessor 64 transmits the signal, via a data communication bus 72, to the digital controller 74, which then transmits the signal through the output amplifier 96 to the mammalian heart 8 via pacing lead 41. The electrical signal transmitted to the "paced" atrium stimulates the "paced" atrium to contract. Additionally, the transmission of the signal to the "paced" atrium, and the subsequent contraction thereof, occurs instantaneously. That is, there is no measurable delay between the steps of detecting the PAC, transmitting the signal from the IMD 10 to the "paced" atrium and contracting the "paced" atrium. At this point, the microprocessor 64 returns to Block 200, to resume the monitoring process, described above, continuing the detection of potential PACs.

The preceding specific embodiments are illustrative of the practice of the invention. It is to be understood, therefore, that other expedients known to those skilled in the art or disclosed herein, may be employed without departing from the invention or the scope of the appended claims. For example, the present invention is not limited to instances of detecting a PAC. The present invention is also not limited to implantable medical devices per se, but may find further application as a medical altering device. The present invention further includes within its scope methods of making and using the algorithm described above.

In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

All printed publications, patent applications and patents referenced hereinabove are incorporated by reference herein, each in its respective entirety.

We claim:

1. A method for instantaneously stimulating a mammalian heart, the mammalian heart including a first atrium and a second atrium, comprising:
   receiving a commencement signal;
   receiving at least one additional signal;
   measuring a plurality of intervals corresponding to the time between two successive signals;
   calculating an average interval;
   comparing one of the plurality of intervals to the average interval; and
   when a difference between the average interval and one of the plurality of intervals is greater than a predetermined time period, instantaneously transmitting a contraction signal to the second atrium.

2. The method of claim 1, wherein the commencement signal is transmitted from the first atrium.

3. The method of claim 1, wherein each of the at least one additional signals is sent from the first atrium.

4. The method of claim 1, wherein the average interval is a function of at least two of the plurality of intervals.

5. The method of claim 1, wherein the contraction signal includes an instruction to stimulate the second atrium to contract.

6. The method of claim 1, wherein the mammalian heart is a human heart.

7. The method of claim 1, wherein the first atrium is the left atrium.

8. The method of claim 1, wherein the first atrium is the right atrium.

9. The method of claim 1, wherein the second atrium is the left atrium.

10. The method of claim 1, wherein the second atrium is the right atrium.

11. The method of claim 1, wherein the predetermined time period corresponds to fifteen successive beats per minute of the mammalian heart.

12. The method of claim 1, wherein the contraction signal comprises an electrical current.

13. An implantable medical device, comprising:
   a processor;
   a controller operably connected to the processor;
   at least one sensing lead operably connected to the controller; and
   at least one pacing lead operably connected to the controller; wherein
   a signal is instantaneously sent from the controller to one of the at least one pacing leads to contract a paced atrium when at least one interval calculated from at least two signals received from a sensed atrium via one of the at least one sensing leads is less than an average interval by a predetermined time factor.

14. The implantable medical device of claim 13, wherein each of the at least one sensing leads has one end, the one end being positioned in the sensed atrium.

15. The implantable medical device of claim 13, wherein each of the at least one pacing leads has one end, the one end being positioned in the paced atrium.

16. The implantable medical device of claim 13, wherein the average interval corresponds to the average of at least two intervals.

17. The implantable medical device of claim 13, wherein the signal includes an instruction to stimulate the paced atrium to contract.

18. The implantable medical device of claim 13, wherein the paced atrium is a left atrium of a mammalian heart.

19. The implantable medical device of claim 13, wherein the paced atrium is a right atrium of a mammalian heart.

20. The implantable medical device of claim 13, wherein the sensed atrium is a left atrium of a mammalian heart.

21. The implantable medical device of claim 13, wherein the sensed atrium is a right atrium of a mammalian heart.

22. The implantable medical device of claim 13, wherein the predetermined time period corresponds to fifteen successive beats per minute of a mammalian heart.

23. The implantable medical device of claim 13, wherein the signal comprises an electrical current.

24. The implantable medical device of claim 13, wherein each of the at least one sensing leads further includes at least one electrode disposed at the distal end of each of the at least one sensing leads.

25. The implantable medical device of claim 13, wherein each of the at least one pacing leads further includes at least one electrode disposed at the distal end of each of the at least one pacing leads.

26. The implantable medical device of claim 13, further including an output pulse generator operably connected to the controller.

27. The implantable medical device of claim 13, wherein the output pulse generator generates the signal.

28. The implantable medical device of claim 13, further including a sense measurement unit operably connected to the controller.

29. The implantable medical device of claim 13, wherein the sense measurement unit receives each of the signals from each of the at least one sensing leads.

30. An implantable medical device system for instantaneously stimulating a mammalian heart, the mammalian heart including a first atrium and a second atrium, comprising:
   means for receiving a commencement signal;
   means for receiving at least one additional signal;
   means for measuring a plurality of intervals corresponding to the time between two successive signals;
   means for calculating an average interval;
   means for comparing one of the plurality of intervals to the average interval; and
   when a difference between the average interval and one of the plurality of intervals is greater than a predetermined time period, means for instantaneously transmitting a contraction signal to the second atrium.

31. The implantable medical device system of claim 30, wherein the commencement signal is transmitted from the first atrium.

32. The implantable medical device system of claim 30, wherein each of the at least one additional signals is sent from the first atrium.

33. The implantable medical device system of claim 30, wherein the average interval is a function of at least two of the plurality of intervals.

34. The implantable medical device system of claim 30, wherein the contraction signal includes an instruction to stimulate the second atrium to contract.

35. The implantable medical device system of claim 30, wherein the mammalian heart is a human heart.

36. The implantable medical device system of claim 30, wherein the first atrium is the left atrium.

37. The implantable medical device system of claim 30, wherein the first atrium is the right atrium.

38. The implantable medical device system of claim 30, wherein the second atrium is the left atrium.

39. The implantable medical device system of claim 30, wherein the second atrium is the right atrium.

40. The implantable medical device system of claim 30, wherein the predetermined time period corresponds to fifteen successive beats per minute of the mammalian heart.

41. The implantable medical device system of claim 30, wherein the contraction signal comprises an electrical current.

42. A method for instantaneously stimulating a mammalian heart, the mammalian heart including a left atrium and a right atrium, comprising:

receiving a commencement signal;

receiving at least one additional signal;

measuring a plurality of intervals corresponding to the time between two successive signals;

calculating an average interval;

comparing one of the plurality of intervals to the average interval; and when a difference between the average interval and one of the plurality of intervals is greater than a predetermined time period, transmitting a contraction signal to the left atrium.

43. The method of claim 42, wherein the commencement signal is transmitted from the right atrium.

44. The method of claim 42, wherein each of the at least one additional signals is sent from the right atrium.

45. The method of claim 42, wherein the average interval is a function of at least two of the plurality of intervals.

46. The method of claim 42, wherein the contraction signal includes an instruction to stimulate the left atrium to contract.

47. The method of claim 42, wherein the mammalian heart is a human heart.

48. The method of claim 42, wherein the predetermined time period corresponds to fifteen successive beats per minute of the mammalian heart.

49. The method of claim 1, wherein the contraction signal comprises an electrical current.

50. The method of claim 1, wherein the contraction signal is transmitted instantaneously.

* * * * *